(12) United States Patent
Alstermark Lindstedt et al.

(10) Patent No.: US 7,276,539 B2
(45) Date of Patent: Oct. 2, 2007

(54) 3-PHENYL-2-ARYLALKYLTHIOPROPIONIC ACID DERIVATIVES AS SELECTIVE AGONISTS OF PPAR-ALPHA

(75) Inventors: Eva-Lotte Alstermark Lindstedt, Molndal (SE); Anna Maria Persdotter Boije, Molndal (SE); Patrick Holm, Molndal (SE)

(73) Assignee: AstraZeneca AB, Sodertalje (SE)

( * ) Notice: Subject to any disclaimer, the term of this patent is extended or adjusted under 35 U.S.C. 154(b) by 93 days.

(21) Appl. No.: 10/499,042

(22) PCT Filed: Dec. 18, 2002

(86) PCT No.: PCT/GB02/05743

§ 371 (c)(1),
(2), (4) Date: Mar. 28, 2005

(87) PCT Pub. No.: WO03/051826

PCT Pub. Date: Jun. 26, 2003

(65) Prior Publication Data

US 2005/0215630 A1    Sep. 29, 2005

(30) Foreign Application Priority Data

Dec. 19, 2001  (SE) .................... 0104333

(51) Int. Cl.
*A61K 31/10* (2006.01)
*C07C 309/66* (2006.01)

(52) U.S. Cl. ........................... 514/709; 558/52
(58) Field of Classification Search ............ 558/52
See application file for complete search history.

(56) References Cited

U.S. PATENT DOCUMENTS

| 5,232,945 | A | 8/1993 | Hulin | |
| 5,306,726 | A | 4/1994 | Hulin | |
| 6,884,821 | B1 | 4/2005 | Shinoda et al. | 514/563 |
| 6,906,058 | B2 | 6/2005 | Starke et al. | |
| 7,125,864 | B2 | 10/2006 | Starke et al. | |
| 7,132,416 | B2 | 11/2006 | Starke et al. | |
| 2004/0102634 | A1 | 5/2004 | Matsuura et al. | 546/218 |

FOREIGN PATENT DOCUMENTS

| EP | 1216980 | 6/2002 |
| EP | 1380562 | 1/2004 |
| SE | 9801990-4 | 6/1998 |
| WO | 91/19702 | 12/1991 |
| WO | 99/29640 | 6/1999 |
| WO | 99/62871 | 9/1999 |
| WO | 99/62872 | 9/1999 |
| WO | 99/62871 A | 12/1999 |
| WO | 99/62872 A | 12/1999 |
| WO | 00/64888 | 11/2000 |
| WO | 01/25181 | 4/2001 |
| WO | WO 01/25181 | 4/2001 |
| WO | 01/40170 | 6/2001 |
| WO | 01/40172 | 6/2001 |
| WO | 01/66098 | 9/2001 |
| WO | WO 01/66533 | 9/2001 |
| WO | WO 02/32428 | 4/2002 |
| WO | WO 02/50051 | 6/2002 |
| WO | 02/096863 | 12/2002 |
| WO | 02/100812 | 12/2002 |
| WO | WO 02/100812 | 12/2002 |
| WO | WO 03/020710 | 3/2003 |
| WO | WO 03/022286 | 3/2003 |
| WO | WO 03/022825 | 3/2003 |
| WO | WO 03/022830 | 3/2003 |
| WO | WO 03/051821 | 6/2003 |
| WO | WO 03/051822 | 6/2003 |
| WO | WO 03/091232 | 11/2003 |
| WO | WO 03/106482 | 12/2003 |
| WO | WO 2004/000294 | 12/2003 |
| WO | WO 2004/000295 | 12/2003 |
| WO | WO 2004/000790 | 12/2003 |
| WO | WO 2004/056748 | 6/2004 |
| WO | WO 2004/110984 | 12/2004 |
| WO | WO 2004/110985 | 12/2004 |
| WO | WO 2004/113276 | 12/2004 |
| WO | WO 2004/113282 | 12/2004 |
| WO | WO 2004/113283 | * 12/2004 |
| WO | WO 2004/113284 | 12/2004 |
| WO | WO 2004/113285 | 12/2004 |

\* cited by examiner

OTHER PUBLICATIONS

Willson et al., J Med. Chem. Feb. 24, 2000, vol. 43, pp. 527-550.
Cronet et al., Structure, Aug. 2001, vol. 9, pp. 699-706.

*Primary Examiner*—Joseph K. McKane
*Assistant Examiner*—Andrew B. Freistein
(74) *Attorney, Agent, or Firm*—Morgan Lewis & Bockius LLP

(57) ABSTRACT

A compound of formula I

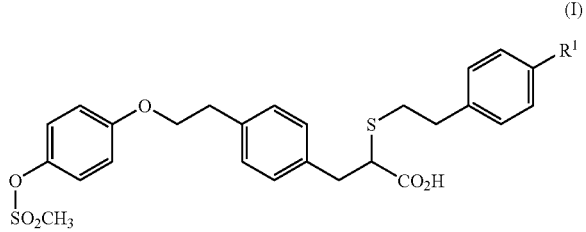

wherein $R^1$ represents chloro, fluoro or hydroxy as well as optical isomers and racemates thereof as well as pharmaceutically acceptable salts, prodrugs, solvates and crystalline forms thereof, processes for preparing such compounds, their utility in treating clinical conditions associated with insulin resistance, methods for their therapeutic use and pharmaceutical compositions containing them.

18 Claims, No Drawings

3-PHENYL-2-ARYLALKYLTHIOPROPIONIC ACID DERIVATIVES AS SELECTIVE AGONISTS OF PPAR-ALPHA

This application is a national stage filing under 35 U.S.C. § 371 of PCT/GB02/05743, filed Dec. 18, 2002 and claims foreign priority from Sweden patent application no. 0104333-0, filed Dec. 19, 2001.

FIELD OF THE INVENTION

The present invention relates to certain novel 3-phenyl-2-arylalkylthiopropionic acid derivatives, to processes for preparing such compounds, to their utility in treating clinical conditions including lipid disorders (dyslipidemias) whether or not associated with insulin resistance and other manifestations of the metabolic syndrome, to methods for their therapeutic use and to pharmaceutical compositions containing them.

BACKGROUND OF THE INVENTION

The metabolic syndrome including type 2 diabetes mellitus, refers to a cluster of manifestations including insulin resistance with accompanying hyperinsulinaemia, possibly type 2 diabetes mellitus, arterial hypertension, central (visceral) obesity, dyslipidaemia observed as deranged lipoprotein levels typically characterised by elevated VLDL (very low density lipoproteins), small dense LDL particles and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in patients with the metabolic syndrome and thus to correct the dyslipidaemia which is considered to cause the accelerated progress of atherosclerosis. However, currently this is not a universally accepted diagnosis with well-defined pharmacotherapeutic indications.

The S-enantiomer of the compound of formula C below

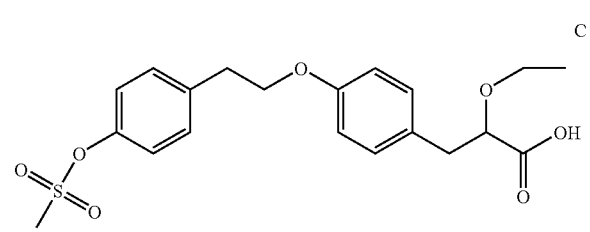

C 2-ethoxy-3-[4-(2-{4-methanesulfonyloxyphenyl}ethoxy)phenyl]propanoic acid, is disclosed in PCT Publication Number WO99/62872. This compound is reported to be a modulator of peroxisome proliferator-activated receptors (PPAR, for a review of the PPARs see T. M. Willson et al, J Med Chem 2000, Vol 43, 527) and has combined PPARα/PPARγ agonist activity (Structure, 2001, Vol 9, 699, P. Cronet et al). This compound is effective in treating conditions associated with insulin resistance.

Surprisingly a series of compounds has now been found which are selective PPARα modulators.

DESCRIPTION OF THE INVENTION

The present invention provides a compound of formula I

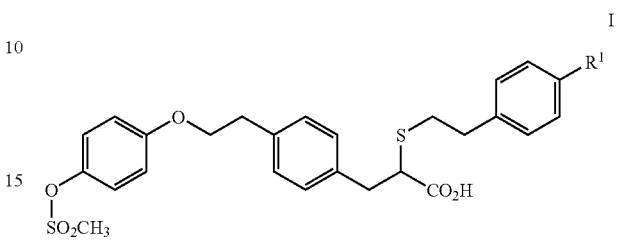

I wherein $R^1$ represents chloro, fluoro or hydroxy as well as optical isomers and racemates thereof as well as pharmaceutically acceptable salts, prodrugs, solvates and crystalline forms thereof.

It will be appreciated by those skilled in the art the compounds of formula I contain an optically active centre and therefore can exist as enantiomers which can be separated as described later. It is expected that most, if not all, of the activity of the compounds of formula I resides in one enantiomer: either the S or the R enantiomer or the (+) or the (−) enantiomer. The enantiomers which are more active in the assays which are described later are preferred forms of the present invention. It will be understood that the present invention includes all mixtures of this active enantiomer with the other enantiomer, for example the racemic mixture, which is a useful intermediate for the active enantiomer.

The active enantiomers may be isolated by separation of racemate for example by fractional crystallization, resolution of HPLC on a chiral column (for example a Chiralpak™ AD 250×50 column). Alternatively the active enatiomers may be made by chiral synthesis from chiral starting materials under conditions which will not cause racemisation or epimerisation, or by derivatisation with a chiral reagent.

The term "prodrug" as used in this specification includes derivatives of the carboxylic acid group which are converted in a mammal, particularly a human, into the carboxylic acid group or a salt or conjugate thereof. The term "prodrug" also includes derivatives of the is hydroxy substituent (when $R^1$ represents hydroxy) which are converted in a mammal, particularly a human, into the hydroxy group or a salt or conjugate thereof. It should be understood that, whilst not being bound by theory, it is believed that most of the activity associated with the prodrugs arises from the activity of the compound of formula I into which the prodrugs are converted. Prodrugs can be prepared by routine methodology well within the capabilities of someone skilled in the art. Various prodrugs of carboxy and hydroxy are known in the art. For examples of such prodrug derivatives, see:

a) Design of Prodrugs, edited by H. Bundgaard, (Elsevier, 1985) and Methods in Enzymology. 42: 309–396, edited by K. Widder, et al. (Academic Press, 1985);

b) A Textbook of Drug Design and Development, edited by Krogsgaard-Larsen and

H. Bundgaard, Chapter 5 "Design and Application of Prodrugs", by H. Bundgaard p. 113–191 (1991);

c) H. Bundgaard, Advanced Drug Delivery Reviews, 8:1–38 (1992);

d) H. Bundgaard, et al., Journal of Pharmaceutical Sciences, 77:285 (1988); and
e) N. Kakeya, et al., Chem Pharm Bull, 32:692 (1984).

The above documents a to e are herein incorporated by reference.

In vivo cleavable esters are just one type of prodrug of the parent molecule. An in vivo hydrolysable (or cleavable) ester of a compound of the formula (I) that contains a carboxy or a hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters, for example, methoxymethyl; $C_{1-6}$alkanoyloxymethyl esters, for example, pivaloyloxymethyl; phthalidyl esters; $C_{3-8}$cycloalkoxycarbonyloxy$C_{1-6}$alkyl esters, for example, 1-cyclohexyl-carbonyloxyethyl; 1,3-dioxolen-2-onylmethyl esters, for example, 5-methyl-1,3-dioxolen-2-onlymethyl; and $C_{1-6}$alkoxycarbonyloxyethyl esters, for example, 1-methoxycarbonyloxyethyl; and may be formed at any carboxy group in the compounds of this invention. An in vivo hydrolysable (or cleavable) ester of a compound of the formula (I) that contains a hydroxy group includes inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4- position of the benzoyl ring.

The compounds of formula I have activity as medicaments, in particular the compounds of formula I are selective agonists of PPARα, that is, their $EC_{50}$ for PPARα is at least ten times lower than their respective $EC_{50}$ for PPARγ wherein the $EC_{50}$s are measured and calculated as described in the assays later in this document. The compounds of formula I are potent and selective.

Specific compounds of the invention are:
2-{[2-(4-chlorophenyl)ethyl]thio}-3-[4-(2-{4-[(methylsulfonyl)oxy]-phenoxy}ethyl)phenyl]propanoic acid; preferably either the (R)-enantiomer or the (S)-enantiomer;
2-{[2-(4-hydroxyphenyl)ethyl]thio}-3-[4-(2-{4-[(methylsulfonyl)oxy]-phenoxy}ethyl)phenyl]propanoic acid; preferably either the (R)-enantiomer or the (S)-enantiomer;
2-{[2-(4-fluorophenyl)ethyl]thio}-3-[4-(2-{4-[(methylsulfonyl)oxy]-phenoxy}ethyl)phenyl]propanoic acid; preferably either the (R)-enantiomer or the (S)-enantiomer;
(−)-2-{[2-(4-chlorophenyl)ethyl]thio}-3-[4-(2-{4-[(methylsulfonyl)oxy]-phenoxy}ethyl)phenyl]propanoic acid and
(−)-2-{[2-(4-hydroxyphenyl)ethyl]thio}-3-[4-(2-{4-[(methylsulfonyl)oxy]-phenoxy}ethyl)phenyl]propanoic acid;

and pharmaceutically acceptable salts, prodrugs, solvates and crystalline forms thereof.

It will be understood by those skilled in the art that where (−) occurs in the above list that the compound indicated has a negative rotation when measured using the conditions and concentration described in the experimental section. It should be understood that salts of the parent acid are included even if a particular salt exhibits a (+) rotation provided that the absolute configuration of the salt is the same as the configuration of the (−)-parent acid.

Specific enantiomers of the invention are selected from one or more of the following:
(R)-2-{[2-(4-chlorophenyl)ethyl]thio}-3-[4-(2-{4-[(methylsulfonyl)oxy]-phenoxy}ethyl)phenyl]propanoic acid;
(S)-2-{[2-(4-chlorophenyl)ethyl]thio}-3-[4-(2-{4-[(methylsulfonyl)oxy]-phenoxy}ethyl)phenyl]propanoic acid;
(R)-2-{[2-(4-hydroxyphenyl)ethyl]thio}-3-[4(2-{4-[(methylsulfonyl)oxy]-phenoxy}ethyl)phenyl]propanoic acid;
(S)-2-{[2-(4-hydroxyphenyl)ethyl]thio}-3-[4-(2-{4-[(methylsulfonyl)oxy]-phenoxy}ethyl)phenyl]propanoic acid;
(R)-2-{[2-(4-fluorophenyl)ethyl]thio}-3-[4-(2-{4-[(methylsulfonyl)oxy]-phenoxy }ethyl)phenyl]propanoic acid;
(S)-2-{[2-(4-fluorophenyl)ethyl]thio}-3-[4-(2-{4-[(methylsulfonyl)oxy]-phenoxy}ethyl)phenyl]propanoic acid;
(−)-2-{[2-(4-chlorophenyl)ethyl]thio}-3-[4-(2-{4-[(methylsulfonyl)oxy]-phenoxy}ethyl)phenyl]propanoic acid and
(−)-2-{[2-(4-hydroxyphenyl)ethyl]thio}-3-[4-(2-{4-[(methylsulfonyl)oxy]-phenoxy}ethyl)phenyl]propanoic acid;

and pharmaceutically acceptable salts, solvates and crystalline forms thereof.

In the present specification the expression "pharmaceutically acceptable salts" is intended to define but is not limited to base salts such as the alkali metal salts, alkaline earth metal salts, ammonium salts, salts with basic amino acids, and salts with organic amines.

It will also be understood that certain compounds of the present invention may exist in solvated, for example hydrated, as well as unsolvated forms. It is to be understood that the present invention encompasses all such solvated forms. Certain compounds of the present invention may exist as tautomers. It is to be understood that the present invention encompasses all such tautomers.

Methods of Preparation

The compounds of the invention may be prepared as outlined below. However, the invention is not limited to these methods, the compounds may also be prepared as described for structurally related compounds in the prior art. The reactions can be carried out according to standard procedures or as described in the experimental section.

Compounds of formula I may be prepared by reacting a compound of formula II

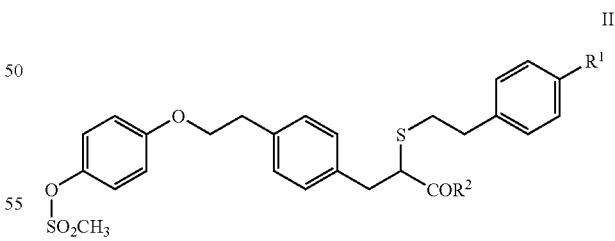

in which $R^1$ is as previously defined and $R^2$ represents a protecting group for carboxylic hydroxy group as described in the standard text "Protective Groups in Organic Synthesis", $2^{nd}$ Edition (1991) by Greene and Wuts, with a deprotecting reagent. The protecting group may also be a resin, such as Wang resin or 2-chlorotrityl chloride resin. Protecting groups may be removed in accordance to techniques which are well known to those skilled in the art. One such protecting group is where $R^2$ represents $C_{1-6}$alkoxy group or an arylalkoxy group eg benzyloxy, such that $COR^2$ represents an ester. Such esters can be reacted with a a deprotecting reagent e.g. a hydrolysing agent, for example lithium hydroxide in a mixture of THF and water, at a temperature in the range of 0–100° C. to give compounds of formula I.

Compounds of formula II may be prepared by reacting a compound of formula III

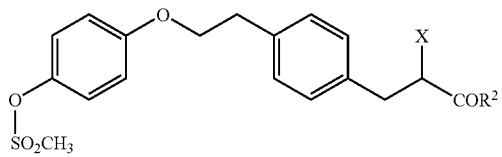

in which $R^2$ is as previously defined and X is a leaving group for example halo e.g. chloro with a compound of formula IV

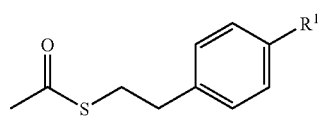

in which $R^1$ is as previously defined or a protected hydroxy group for example $R^1$ is benzyloxy.

Compounds of formula III and IV may be prepared by methods described in the Examples or by analogous methods known to those skilled in the art.

Compounds of formula II, III and IV are believed to be novel and are claimed herein as useful intermediates in the preparation of compounds of formula I.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutical acceptable organic or inorganic base addition salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001–100 mg/kg body weight, preferably 0.001–10 mg/kg body weight.

Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are useful for the prophylaxis and/or treatment of clinical conditions associated with inherent or induced reduced sensitivity to insulin (insulin resistance) and associated metabolic disorders (also known as metabolic syndrome). These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAI particle levels and high Apo B levels in the presence of small, dense, low density lipoproteins (LDL) particles, phenotype B.

The compounds of the present invention are expected to be useful in treating patients with combined or mixed hyperlipidemias or various degrees of hypertriglyceridemias and postprandial dyslipidemia with or without other manifestations of the metabolic syndrome.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of formula I to a mammal (particularly a human) in need thereof.

The present invention provides a method of treating or preventing type 2 diabetes comprising the administration of an effective amount of a compound of formula I to a mammal (particularly a human) in need thereof.

In a further aspect the present invention provides the use of a compound of formula I as a medicament.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of formula I to a mammal (particularly a human) in need thereof.

The present invention provides a method of treating or preventing type 2 diabetes comprising the administration of an effective amount of a compound of formula I to a mammal (particularly a human) in need thereof.

In a further aspect the present invention provides the use of a compound of formula I as a medicament.

In a further aspect the present invention provides the use of a compound of formula I in the manufacture of a medicament for the treatment of insulin resistance and/or metabolic disorders.

Combination Therapy

The compounds of the invention may be combined with other therapeutic agents that are useful in the treatment of disorders associated with the development and progress of atherosclerosis such as hypertension, hyperlipidaemias, dyslipidaemias, diabetes and obesity. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt, solvate, solvate of such a salt or a prodrug thereof, may be administered in association with another PPAR modulating agent. PPAR modulating agents include but are not limited to a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623–634 (in particular the compounds described in the patent applications listed on page 634) and J Med Chem, 2000, 43, 527 which are all incorporated herein by reference. Particularly a PPAR alpha and/or gamma agonist refers to NN622/Ragaglitazar, BMS 298585, WY-14643, clofibrate, fenofibrate, bezafibrate, gemfibrozil and ciprofibrate; GW 9578, ciglitazone, troglitazone, pioglitazone, rosiglitazone, eglitazone, proglitazone, BRL-49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{methanesulphonyloxyphenyl}ethoxy)-phenyl]propanoic acid and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. A more particular statin is atorvastatin calcium salt. A particularly preferred statin is, however, a compound with the chemical name (E)-7-[4-(4-fluorophenyl)-6-isopropyl-2-[methyl(methylsulfonyl)- amino]-pyrimidin-5-yl](3R,5S)-3,5-dihydroxyhept-6-enoic acid, [also known as (E)-7-[4-(4-fluorophenyl)-6-isopropyl-2-[N-methyl-N-(methylsulfonyl)-amino]pyrimidin-5-yl](3R,5S)-3,5-dihydroxyhept-6-enoic acid] or a pharmaceutically acceptable salt or solvate thereof, or a solvate of such a salt. The compound (E)-7-[4-(4-fluorophenyl)-6-isopropyl-2-[methyl-(methylsulfonyl)-amino]-pyrimidin-5-yl](3R,5S)-3,5-dihydroxyhept-6-enoic acid, and its calcium and sodium salts are disclosed in European Patent Application, Publication No. EP-A-0521471, and in Bioorganic and Medicinal Chemistry, (1997), 5(2), 437–444. This latter statin is now known under its generic name rosuvastatin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with an inhibitor of the ileal bile acid transport system (13AT inhibitor).

Suitable compounds possessing 1BAT inhibitory activity have been described, see for instance the compounds described in WO 93/16055, WO 94/18183, WO 94/18184, WO 96/05188, WO 96/08484, WO 96/16051, WO 97/33882, WO 98/07449, WO 98/03818, WO 98/38182, WO 99/32478, WO 99/35135, WO 98/40375, WO 99/35153, WO 99/64409, WO 99/64410, WO 00/01687, WO 00/47568, WO 00/61568, WO 00/62810, WO 01/68906, DE 19825804, WO 00/38725, WO 00/38726, WO 00/38727, WO 00/38728, WO 00/38729, WO 01/68906, WO 01/66533, WO 02/32428, WO 02/50051, EP 864 582, EP489423, EP549967, EP573848, EP624593, EP624594, EP624595 and EP624596 and the contents of these patent applications are incorporated herein by reference.

Particular classes of IBAT inhibitors suitable for use in the present invention are benzothiepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing MBAT inhibitory activity is (3R,5R)-3-butyl-3-ethyl-1,1-dioxido-5-phenyl-2,3,4,5-tetrahydro-1,4-benzothiazepin-8-ylβ-D-glucopyranosiduronic acid (EP 864 582). Other suitable IBAT inhibitors include one of:

1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{(N-[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzy}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthio-ethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl }-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxy-hexyl)carbamoyl]-4-hydroxybenzyl}carbamoylmethoxy)-2,3,4,5-tetrahydro-1,2,5-benzothiadiazepine; and 1,1-Dioxo-3,3-dibutyl-5-phenyl-7-methylthio-8-(N-{(R)-α-[N-(2-(S)-3-(R)-4)-(R)-5-(R)-2,3,4,5,6-pentahydroxy-hexyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

According to an additional further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22-page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751–54, 1998 which are incorporated herein by reference;

a nicotinic acid derivative, including slow release and combination products, for example, nicotinic acid (niacin), acipimox and niceritrol;

a phytosterol compound for example stanols; probucol;

an anti-obesity compound for example orlistat (EP 129, 748) and sibutramine (GB 2,184,122 and U.S. Pat. No. 4,929,629);

an antihypertensive compound for example an angiotensin converting enzyme (ACE) inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, an AT-1 blocker, a saluretic, a diuretic or a vasodilator;

a CB1 antagonist or inverse agonist for example as described in WO01/70700 and EP 65635;

a Melanin concentrating hormone (MCH) antagonist;

a PDK inhibitor; or modulators of nuclear receptors for example LXR, FXR, RXR, and RORalpha; or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula I include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula I include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

Therefore in an additional feature of the invention, there is provided a method for for the treatment of type 2 diabetes and its associated complications in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof.

According to a further aspect of the present invention there is provided a kit comprising:
a) a compound of formula I, or a pharmaceutically acceptable salt, solvate, solvate of such a salt or a prodrug thereof, in a first unit dosage form;
b) one of the other compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula I, or a pharmaceutically acceptable salt, solvate, solvate of such a salt or a prodrug thereof, together with a pharmaceutically acceptable diluent or carrier, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the the treatment of metabolic syndrome or type 2 diabetes and its associated complications in a warm-blooded animal, such as man.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

EXAMPLES $^1$H NMR and $^{13}$C NMR measurements were performed on a Varian Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale (δ).

Unless otherwise stated, chemical shifts are given in ppm with the solvent as internal standard.

| Abbreviations | |
|---|---|
| DMSO | dimethyl sulfoxide |
| EtOAc | ethyl acetate |
| DMF | N,N-dimethylformamide |
| THF | tetrahydrofuran |
| MeCN | acetonitrile |
| MeOH | methanol |
| TFA | trifluoroacetic acid |
| NH$_4$OAc | ammonium acetate |
| t | triplet |
| s | singlet |
| d | doublet |
| q | quartet |
| m | multiplet |
| bs | broad singlet |

Example 1

2-{[2-(4-Chlorophenyl)ethyl]thio}-3-[4-(2-{4-[(methylsulfonyl)oxy]phenoxy}ethyl)phenyl]propanoic acid

(i) [2-(4-Chlorophenyl)ethyl]ethanethioate 1-(2-Chloroethyl)-4-chlorobenzene (0.700 g, 4.00 mmol), thioacetic acid (0.320 g, 4.20 mmol) and triethylamine (0,425 g, 4.20 mmol) were dissolved in MeOH (8 ml). The solution was warmed with microwaves for 900 seconds at 150° C. The mixture was used in the next step without purification.

(ii) 2-{[2-(4-Chlorophenyl)ethyl]thio}-3-[4-(2-{4-[(methylsulfonyl)oxy]phenoxy}ethyl)phenyl]propanoic acid The reaction vessel was flushed with argon. To a part 0.8 ml (0.400 mmol) of the mixture from the reaction step above was added under stirring sodium methanethiolate (56.5 mg, is 0.800 mmol) in MeOH (0.2 ml). After an hour methyl 2-chloro-3-[4-(2-{4-[(methylsulfonyl)oxy]phenoxy}ethyl)phenyl]propanoate (0.200 g, 0.484 mmol, prepared as described in Example 2) in acetonitrile (0.800 ml) was added. The mixture was stirred for 16 h under an argon atmosphere and then centrifuged under vacuum at 35° C. 2 ml 0.5 M LiOH solution (THF/water 7:1) was added and the mixture was stirred vigorously for 20 h. After acidification with 12 M HCl (100 µl) the stirring was continued for another hour. The crude product was filtered through a Teflon™ filter and further purified using preparative BPLC (0.2% TFA/MeCN, gradient). The pooled fractions were centrifuged under vacuum giving 18 mg of the desired product (yield 7%).

$^1$H-NMR (400 MHz, CDCl$_3$): 2.75–2.95 (m, 5H), 3.06 (t, 2H), 3.10 (s, 3H), 3.16 (dd, 1H), 3.45 (dd, 1H), 4.14 (d, 2H), 6.87 (d, 2H), 7.05 (d, 2H), 7.11–7.27 (m, 8H).

(iii) (−)-2-{[2-(4-chlorophenyl)ethyl]thio }-3-[4-(2-{4-[(methylsulfonyl)oxy]-phenoxy}ethyl)phenyl]propanoic acid The (−)-enantiomer of 2-{[2-(4-chlorophenyl)ethyl]thio}-3-[4-(2-{4-[(methylsulfonyl)-oxy]phenoxy}ethyl)phenyl]propanoic acid was separated from the racemate by chiral chromatography. A Chiralpak AD JF003 (250×20 mm i.d.) column was used and ethanol/formic acid 100/0.1% as mobile phase. The racemate (2 g) was dissolved in ethanol (20 mg/ml) and was injected onto the column. The first eluting peak was collected and UV-detected. The product (0.9 g) was obtained with an enantiomeric purity=99.2%. The optical rotation was found to be $[\alpha]^{20}_D=-29°$ by dissolving the enantiomer in ethanol to give a concentration of 0.5 g/100 ml. The optical rotation was measured at 20° C. using the sodium line at 589 nm.

$^1$H NMR (500 MHz, CD$_3$OD): 7.18–7.25 (6H, m), 7.15 (2H, d), 7.13 (2H, d), 4.16 (2H, t), 3.45 (1H, t), 3.14 (3H, s), 3.11 (1H, m), 3.04(2H, t), 2.77–2.90 (5H, m).

Example 2

2-{[2-(4-Hydroxyphenyl)ethyl]thio}-3-[4-(2-{4-[(methylsulfonyl)oxy]phenoxy}ethyl)phenyl]propanoic acid

(i) Methyl 2-chloro-3-[4-(2-hydroxyethyl)phenyl]propanoate 2-(4-Aminophenyl)ethanol (11 g, 81 mmol) and 32 ml conc HCl was dissolved in acetone and cooled to 0° C. Sodium nitrite (5.6 g, 81 mmol) in 20 ml water was added dropwise. The temperature was kept under 0° C. After one hour, methyl acrylate (70 g, 808 mmol) and CuI (1.6 g, 8 mmol) were added (<0° C.). The reaction mixture was stirred at room temperature overnight.

The solvent was evaporated and water was added. The water phase was extracted three times with EtOAc, the organic phases were pooled and washed with water, dried (MgSO$_4$) and evaporated under reduced pressure. The crude product was purified by flash chromatography using a 65:35 mixture of EtOAc and heptane as eluent. Further purification by preparative HPLC (using a gradient of CH$_3$CN/5% CH$_3$CN-waterphase containing 0.1M NH$_4$OAc as eluent) gave 9.7 g product (yield 49%) as an oil.

$^1$HNMR (400 MHz, CDCl$_3$): 2.84 (t, 3H), 3.15 (dd, 1H), 3.35 (dd, 1H), 3.75 (s, 3H), 3.84 (t, 3H), 4.43 (t, 1H), 7.17 (d, 4H)

(ii) Methyl 3-(4-{2-[4-(benzyloxy)phenoxy]ethyl}phenyl)-2-chloropropanoate

Triphenylphosphine (2.4 g, 9 mmol) was added to a solution of methyl 2-chloro-3-[4-(2-hydroxyethyl)phenyl]propanoate (2.1 g, 8.5 mmol) and 4-(benzyloxy)phenol (1.7 g, 8 mmol) in 20 ml toluene under nitrogen atmosphere. The solution was warmed to 55° C. and diisopropyl azodicarboxylate (1.8 g, 9 mmol) was added. The reaction mixture was stirred at 55° C. overnight.

The mixture was allowed to cool and the solvent was evaporated under reduced pressure. The crude product was purified by flash chromatography using a 80:20 mixture of heptane and EtOAc as eluent to yield 2.28 g of the desired product (yield 61%) as colourless crystals.

$^1$HNMR (400 MHz, CDCl$_3$): 3.05 (t, 2H), 3.16 (dd, 1H), 3.36 (dd, 1H), 3.75 (s, 3H), 4.12 (t, 2H), 4.45 (t, 1H), 5.01 (s, 2H), 6.82 (m, 2H), 6.90 (m, 2H), 7.13–7.27 (m, 4H), 7.29–7.47 (m, 5H).

(iii) Methyl 2-chloro-3-{4-[2-(4-hydroxyphenoxy)ethyl]phenyl}propanoate

Methyl 3-(4-{2-[4-(benzyloxy)phenoxy]ethyl}phenyl)-2-chloropropanoate (1.0 g, 2.4 mmol) and dimethyl sulfide (0.9 g, 14 mmol) was dissolved in 60 ml CH$_2$Cl$_2$. Boron trifluoride etherate (2.0 g, 14 mmol) was added droppwise to the stirred solution. The reaction mixture was stirred for two days at room temperature. Another equivalent (0.4 g, 2.87 mmol) boron trifluoride etherate was added and the stirring was continued overnight. Water was added. The phases were separated and the aqueous phase was extracted twice with CH$_2$Cl$_2$. The organic phases were pooled, washed (water, brine), dried (Na$_2$SO$_4$) and evaporated under reduced pressure. Further purification by preparative HPLC using a gradient of CH$_3$CN/5% CH$_3$CN-waterphase containing 0.1M NH$_4$OAc gave 0.55 g of the desired product (yield 52%) as an oil.

¹HNMR (400 M&, CDCl₃): 3.04 (t, 2H), 3.16 (dd, 1H), 3.35 (dd, 1H), 3.75 (s, 3H), 4.10 (t, 2H), 4.40 (t, 1H), 6.75 (m, 4H), 7.12–7.29 (m, 4H).

(iv) Methyl 2-chloro-3-[4-(2-{4-[(methylsulfonyl)oxy]phenoxy}ethyl)phenyl]propanoate Methyl 2-chloro-3-{4-[2-(4-hydroxyphenoxy)ethyl]phenyl}propanoate (334 mg, 1.0 mmol) and triethylamine (303 mg, 3.0 mmol) was dissolved in 20 ml dichlormethane and cooled to −20° C. under nitrogen atmosphere. Methanesulfonyl chloride (114 mg, 1.0 mmol) was added dropwise. The mixture was allowed to reach room temperature. After 2 hours dichlormethane was added, the mixture was washed (water, brine), dried (Na₂SO₄) and evaporated under reduced pressure to yield 394 mg pure product (yield 96%).

¹HNMR (400 MHz, CDCl₃): 3.02–3.11 (m, 5H), 3.15 (dd, 1H), 3.35 (dd, 1H), 3.74 (s, 3H), 4.14 (t, 2H), 4.44 (t, 1H), 5.29 (s, 2H), 6.88 (d, 2H), 7.14–7.25 (m, 6H).

(v) Methyl 2-({2-[4-(benzyloxy)phenyl]ethyl}thio)-3-[4-(2-{4-[(methylsulfonyl)oxy]phenoxy}ethyl)phenyl]propanoate 2-[4-(Benzyloxy)phenyl]ethanethiol (334 mg, 1.4 mmol), methyl 2-chloro-3-[4-(2-{4-[(methylsulfonyl)oxy]phenoxy}ethyl)phenyl]propanoate (394 mg, 0.95 mmol) and potassium carbonate (189 mg, 1.4 mmol) were dissolved in 14 ml dry DMF. and stirred under nitrogen atmosphere at room temperature overnight.

The solvent was evaporated under reduced pressure and the residue was dissolved in toluene. The organic phase was washed (water, brine), dried (MgSO₄) and evaporated. Further purification by preparative HPLC using a gradient of CH₃CN/5% CH₃CN-waterphase containing 0.1M NH₄OAc gave 477 mg of the desired product (yield 75%).

¹HNMR (400 MHz, CDCl₃): 2.76–2.89 (m, 4H), 2.95 (dd, 1H), 3.09 (m, 5H), 3.20 (dd, 1H), 3.53 (m, 1H), 3.70 (s, 3H), 4.15 (t, 2H), 5.06 (s, 2H), 6.91 (m, 4H), 7.07–7.24 (m, 8H), 7.31–7.48 (m, 5H).

(vi) Methyl 2-{[2-(4-hydroxyphenyl)ethyl]thio }-3-[4-(2-{4-[(methylsulfonyl)oxy]phenoxy}ethyl)phenyl]propanoate To a solution of methyl 2-({2-[4-(benzyloxy)phenyl]ethyl}thio)-3-[4-(2-{4-[(methylsulfonyl)oxy]phenoxy}ethyl)phenyl]propanoate (477 mg, 0.8 mmol) and 15 ml dichlormethane, dimethyl sulfide (239 mg, 3.8 mol) and boron trifluoride etherate (545 mg, 3.8 mmol) were added. After 18 hours of stirring water was added to the reaction. The phases were separated and the aqueous phase was extracted twice with dichlormethane. The organic phases were pooled, dried (MgSO₄) and evaporated under reduced pressure. 274 mg of the desired product (yield 67%) was obtained as an oil.

¹HNMR (400 MHz, CDCl₃): 2.70–2.85 (m, 4H), 2.91 (dd, 1H), 3.05 (t, 2H), 3.10 (s, 3H), 3.17 (dd, 1H), 3.49 (m, 1H), 3.68 (s, 3H), 4.13 (t, 2H), 6.72 (d, 2H), 6.87 (d, 2H), 6.99 (d, 2H), 7.10–7.22 (m, 6H)

(vii) 2-{[2-(4-Hydroxyphenyl)ethyl]thio}-3-[4-(2-{4-[(methylsulfonyl)oxy]-phenoxy}ethyl)phenyl] propanoic acid Methyl 2-{[2-(4-hydroxyphenyl)ethyl]thio}-3-[4-(2-{4-[(methylsulfonyl)oxy]phenoxy}-ethyl)phenyl]propanoate (105 mg, 0.2 mmol) was dissolved in 6.5 ml of a 7:1 mixture of THF and water and cooled on an ice-bath. Lithium hydroxide (9.4 mg, 0.4 mmol) was added. Water was added to the reaction mixture after 24 hours of stirring at room temperature. The THF was evaporated under reduced pressure and the residue was acidified with 1M hydrochloric acid. The water phase was extracted with EtOAc (×3), the organic phases were pooled, washed (water, brine), dried (MgSO₄) and evaporated. The crude product was purified using preparative HPLC (eluent: CH₃CN/5% CH₃CN-waterphase containing 0.1M NH₄OAc) to give 74 mg of the desired product (yield 97%) as an oil.

¹HNMR (400 MHz, CDCl₃): 2.68–2.95 (m, 5H), 3.05 (t, 2H), 3.10 (s, 3H), 3.17 (dd, 1H), 3.47 (m, 1H), 4.12 (t, 2H), 6.70 (d, 2H), 6.86 (d, 2H), 6.97 (d, 2H), 7.12–7.21 (m, 6H).

¹³CNMR (100 MHz, CDCl₃): 33.8, 35.1, 35.5, 37.2, 37.3, 48.1, 69.3, 115.6, 115.8, 123.3, 129.3, 129.4, 129.9, 132.3, 136.2, 136.9, 142.8, 154.4, 158.0, 177.2.

(viii) (−)-2-{[2-(4-hydroxyphenyl)ethyl]thio}-3-[4-(2-{4-[(methylsulfonyl)oxy]phenoxy}ethyl)phenyl] propanoic acid The racemate of 2-{[2-(4-hydroxyphenyl)ethyl]thio}-3-[4-(2-{4-[(methylsulfonyl)-oxy]phenoxy}ethyl)phenyl]propanoic acid was separated into its enantiomers using chiral chromatography. A Chiralpak AD JDB01+AS003 (336×100 mm i.d.) and ethanol/formic acid 100/0.01% was used as mobile phase. The racemate (9 g) was dissolved in ethanol and injected onto the column. The first eluting peak was collected and UV-detected. The product (4.1 g) was obtained with an enantiomeric purity>99%. The optical rotation was found to be $[\alpha]^{20}{}_D = -33°$ by dissolving the enantiomer in methanol to give a concentration of 0.64 g/100 ml. The optical rotation was measured at 20° C. using the sodium line at 589 nm.

¹H NMR (500 MHz, CD₃OD): 7.17–7.22 (6H, m), 6.99 (2H, d), 6.94 (2H, d), 6.69 (2H, d), 4.17 (2H, t), 3.46 (1H, t), 3.16 (3H, s), 3.13 (1H, dd), 3.05 (2H, t), 2.69–2.88 (5H, m).

Example 3

2-{[2-(4-Fluorophenyl)ethyl]thio}-3-[4-(2-{4-[(methylsulfonyl)oxy]phenoxy}-ethyl)phenyl]propanoic acid

(i) [2-(4-fluorophenyl)ethyl]ethanethioate

To a solution of DMF (60 ml) and thioacetic acid (2.1 g, 28 mmol), cooled in an ice-bath, was added cesium carbonate (9.1 g, 28 mmol). The reaction mixture immediately turned orange. 1-(2-Chloroethyl)-4-fluorobenzene (4 g, 25 mmol) was added, the ice-bath was removed and the reaction was stirred overnight. The solvent was evaporated and the residue was dissolved in EtOAc. The organic phase was washed (water), dried (NaSO₄) and evaporated under reduced pressure to yield 5 g (99%) of the desired product as an oil.

¹HNMR (400 MHz, CDCl₃): 2.33 (s, 3H), 2.83 (t, 2H), 3.09 (t, 2H), 6.98 (t, 2H), 7.17 (m, 2H).

¹³CNMR (100 MHz, CDCl₃): 30.8, 30.9, 35.3, 115.4, 115.6, 130.2, 130.3, 135.9, 160.7, 195.8.

(ii) Methyl 2-{[2-(4-fluorophenyl)ethyl]thio}-3-[4-(2-{4-[(methylsulfonyl)oxy]phenoxy}-ethyl)phenyl] propanoate

[2-(4-Fluorophenyl)ethyl]ethanethioate (96 mg, 0.48 mmol) was dissolved in 1 ml methanol under nitrogen atmosphere. To this slurry was added sodium methanethiolate (33.9 mg, 0.48 mmol). After 30 minutes of stirring methyl 2-chloro-3-[4-(2-{4-[(methylsulfonyl)-oxy]phenoxy}ethyl)phenyl]propanoate (200 mg, 0.48 mmol) dissolved in 2 ml $CH_3CN$ was added. The resulting mixture was stirred overnight.

The solvent was evaporated and the residue was dissolved in EtOAc. The organic phase was washed (water), dried ($MgSO_4$) and evaporated under reduced pressure.

Further purification by preparative HPLC (using a gradient of $CH_3CN/5\%CH_3CN$-waterphase containing 0.1M $NH_4OAc$) gave 82 mg of the desired product (yield 32%).

$^1$HNMR (500 MHz, $CDCl_3$): 2.82–3.00 (m, 5H), 3.10 (t, 2H), 3.14 (s, 3H), 3.22 (dd, 1H), 3.53 (m, 1H), 3.72 (s, 3H), 4.18 (t, 2H), 6.92 (d, 2H), 7.0 (t, 2H), 7.15 (m, 4H), 7.23 (m, 4H).

(iii) 2-{[2-(4-Fluorophenyl)ethyl]thio}-3-[4-(2-{4-[(methylsulfonyl)oxy]-phenoxy}ethyl)phenyl]propanoic acid Methyl 2-{[2-(4-fluorophenyl)ethyl]thio}-3-[4-(2-{4-[(methylsulfonyl)oxy]-phenoxy}ethyl)phenyl]propanoate (77 mg, 0.14 mmol) was dissolved in 2.5 ml of a 4:1 mixture of THF and water and cooled on an ice-bath. Lithium hydroxide (6.9 mg, 0.29 mmol) was added. Water was added after 2 days of stirring at room temperature. The THF was evaporated under reduced pressure. The aqueous phase was acidified with 1M HCl and extracted with EtOAc three times. The organic phases were pooled, washed (water, brine), dried ($MgSO_4$) and evaporated. The crude product was purified using preparative HPLC (eluent: $CH_3CN/5\%$ $CH_3CN$-waterphase containing 0.1M $NH_4Oac$). 24 mg of the desired product (yield 30%) was obtained as an oil.

$^1$HNMR (500 MHz, $CDCl_3$): 2.82–3.00 (m, 5H), 3.10 (t, 2H), 3.14 (s, 3H), 3.21 (dd, 1H), 3.52 (m, 1H), 4.18 (t, 2H), 6.90 (d, 2H), 6.99 (t, 2H), 7.13 (m, 2H), 7.16–7.26 (m, 6H).

Biological Activity

Formulations

Compounds were dissolved in DMSO to obtain 16 mM stock solutions. Before assays, stock solutions were further diluted in DMSO and culture media.

General Chemicals and Reagents

Luciferase assay reagent was purchased from Packard, USA. Restriction Enzymes were from Boehringer and Vent polymerase from New England Biolabs.

Cell Lines and Cell Culture Conditions

U2-OS, (Osteogenic sarcoma, Human) was purchased from ATCC, USA. Cells were expanded and refrozen in batches from passage number six. Cells were cultured in Dulbecco's modified Eagle medium (DMEM) with 25 mM glucose, 2 mM glutamine or 4 mM L-alanyl-L-glutamine, 10% fetal calf serum, at 5% $CO_2$. Phosphate buffered saline (PBS) without addition of calcium or magnesium was used. All cell culture reagents were from Gibco (USA) and 96-well cell culture plates were purchased from Wallach.

Plasmid Constructs for Heterologous Expression

Standard recombinant DNA techniques were carried out as described by Ausubel (7). The Luciferase reporter vector, pGL5UAS (clone consists of five copies of the GAL4 DNA binding sequence, 5'-CGACGGAGTACTGTCCTC-CGAGCT-3', cloned into the SacI/XhoI sites of pGL3-Promoter (Promega). The SacI/XhoI fragment carrying the UAS sites was constructed using annealed overlapping oligonucleotides.

Expression vectors used are based upon pSG5 (Stratagene). All vectors contain an EcoRI/NheI fragment encoding the DNA binding domain of GAL4 (encoding amino acid positions 1–145 of database accession number P04386) followed by an in-frame fusion to a fragment encoding the nuclear localisation sequence from T antigen of Polyoma Virus. The nuclear localisation sequence was constructed using annealed overlapping oligonucleotides creating NheI/KpnI sticky ends (5'-CTAGCGCTCCTAGAAGAAACG-CAAGGTTGGTAC-3'). The ligand binding domains from human and mouse PPARα and human and mouse PPARγ were PCR amplified as KpnI/BamHI fragments and cloned in frame to the GAL4 DNA binding domain and the nuclear localisation sequence. The sequence of all plasmid constructs used were confirmed by sequencing.

The following expression vectors were used for transient transfections:

| vector | encoded PPAR subtype | sequence reference[1] |
|---|---|---|
| pSGGALhPPa | human PPARα | S74349, nt 625–1530 |
| pSGGALmPPa | murine PPARα | X57638, nt 668–1573 |
| pSGGALhPPg | human PPARγ | U63415, nt 613–1518 |
| pSGGALmPPg | murine PPARγ | U09138, nt 652–1577 |

[1]refers to nucleotide positions of data base entry used to express the ligand binding domain.

Transient Transfections

Frozen stocks of cells from passage number six were thawed and expanded to passage number eight before transfections. Confluent cells were trypsinised, washed and pelleted by centrifugation at 270×g for 2 minutes. The cell pellet was resuspended in cold PBS to a cell concentration of about 18×10$^6$ cells/ml. After addition of DNA, the cell suspension was incubated on ice for approximately 5 minutes before electroporation at 230 V, 960 µF in Biorad's Gene Pulser™ in 0.5 ml batches. A total of 50 µg DNA was added to each batch of 0.5 ml cells, including 2.5 µg expression vector, 25 µg reporter vector and 22.5 µg unspecific DNA (pBluescript, Stratagene).

After electroporation, cells were diluted to a concentration of 320'000 cells/ml in DMEM without phenol red, and approximately 25'000 cells/well were seeded in 96-well plates. In order to allow cells to recover, seeded plates were incubated at 37° C. for 34 hours before addition of test compounds. In assays for PPARα, the cell medium was supplemented with resin-charcoal stripped fetal calf serum (FCS) in order to avoid background activation by fatty acid components of the FCS. The resin-charcoal stripped FCS was produced as follows; for 500 ml of heat-inactivated FCS, 10 g charcoal and 25 g Bio-Rad Analytical Grade Anion Exchange Resin 200–400 mesh were added, and the solution was kept on a magnetic stirrer at room temperature over night. The following day, the FCS was centrifuged and the stripping procedure was repeated for 4–6 hours. After the second treatment, the FCS was centrifuged and filter sterilised in order to remove remnants of charcoal and resin.

Assay Procedure

Stock solutions of compounds in DMSO were diluted in appropriate concentration ranges in master plates. From master plates, compounds were diluted in culture media to obtain test compound solutions for final doses.

After adjustment of the amount of cell medium to 75 µl in each well, 50 µl test compound solution was added. Transiently transfected cells were exposed to compounds for about 24 hours before the luciferase detection assay was performed. For luciferase assays, 100 µl of assay reagent was added manually to each well and plates were left for approximately 20 minutes in order to allow lysis of the cells. After lysis, luciferase activity was measured in a 1420 Multiwell counter, Victor, from Wallach.

Reference Compounds

The IZD pioglitazone was used as reference substance for activation of both human and murine PPARγ. 5,8,11,14-Eicosatetrayonic acid (ETYA) was used as reference substance for human PPARα.

Calculations and Analysis

For calculation of $EC_{50}$ values, a concentration-effect curve was established. Values used were derived from the average of two or three independent measurements (after subtraction of the background average value) and were expressed as the percentage of the maximal activation obtained by the reference compound. Values were plotted against the logarithm of the test compound concentration. $EC_{50}$ values were estimated by linear intercalation between the data points and calculating the concentration required to achieve 50% of the maximal activation obtained by the reference compound.

The compounds of formula I have an $EC_{50}$ of less than 5 µmol/l for PPARA and particular compounds have an $EC_{50}$ of less than 1.0 µmol/l. Additionally in particular compounds the ratio of the $EC_{50}$ (PPARγ): $EC_{50}$ (PPARα) is greater than 25:1. It is believed that this ratio is important with respect to the pharmacological activity of the compounds and to their therapeutic profile.

In addition the compounds of the present invention exhibit improved DMPK (Drug Metabolism and Pharmacokinetic) properties for example they exhibit improved metabolic stability in vitro. The compounds also have a promising toxicological profile.

The invention claimed is:

1. A compound of formula I

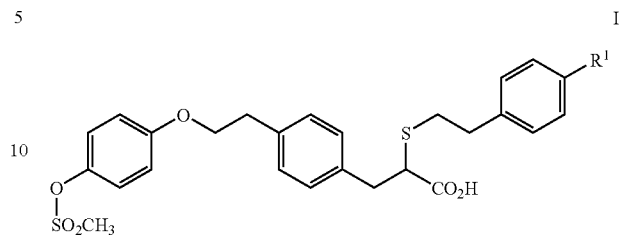

wherein $R^1$ represents chloro, fluoro or hydroxy as well as optical isomers and racemates thereof as well as pharmaceutically acceptable salts, prodrugs, solvates and crystalline forms thereof.

2. A compound selected from

2-{[2-(4-chlorophenyl)ethyl]thio}-3-[4-(2-{4-[(methylsulfonyl)oxy]-phenoxy}ethyl)phenyl]propanoic acid;

2-{[2-(4-hydroxyphenyl)ethyl]thio}-3-[4-(2-{4-[(methylsulfonyl)oxy]-phenoxy}ethyl)phenyl]propanoic acid; and 2-{[2-(4-fluorophenyl)ethyl]thio}-3-[4-(2-{4-[(methylsulfonyl)oxy]-phenoxy}ethyl)phenyl]propanoic acid;

and pharmaceutically acceptable salts, prodrugs, solvates and crystalline forms thereof.

3. The compound (−)-2-{[2-(4-chlorophenyl)ethyl]thio}-3-[4-(2-{4-[(methylsulfonyl)oxy]-phenoxy}ethyl)phenyl]propanoic acid.

4. The compound (−)-2-{[2-(4-hydroxyphenyl)ethyl]thio}-3-[4-(2-{4-[(methylsulfonyl)oxy]-phenoxy}ethyl)phenyl]propanoic acid.

5. The (R)-enantiomer or the (S)-enantiomer of 2-{[2-(4-fluorophenyl)ethyl]thio}-3-[4-(2-{4-[(methylsulfonyl)oxy]-phenoxy}ethyl)phenyl]propanoic acid.

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: GAL4 DNA binding sequence

<400> SEQUENCE: 1
cgacggagta ctgtcctccg agct       24

<210> SEQ ID NO 2
<211> LENGTH: 33
<212> TYPE: DNA
<213> ORGANISM: Artificial Sequence
<220> FEATURE:
<223> OTHER INFORMATION: Nuclear localization sequence

<400> SEQUENCE: 2
ctagcgctcc tagaagaaac gcaaggttgg tac       33

6. A pharmaceutical formulation comprising a compound according to any one of claim 1 to 5 in admixture with pharmaceutically acceptable adjuvants, dilutents and/or carriers.

7. A method of treating dyslipidemia comprising the administration of a compound according to any one of claim 1–5 to a mammal in need thereof.

8. A method of treating type 2 diabetes comprising the administration of an effective amount of a compound of formula I according to any one of claim 1–5 to a mammal in need thereof.

9. A process for preparing a compound of formula I as defined in claim 1 comprising reacting a compound of formula II

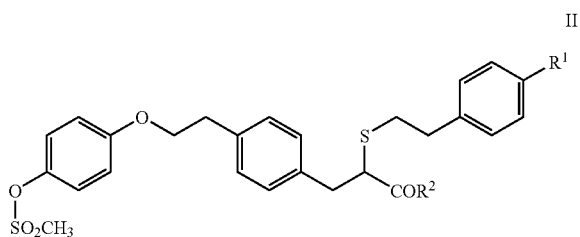

in which $R^1$ is as defined in claim 1 and $R^2$ represents a protecting group for a carboxylic hydroxy group with a de-protecting reagent.

10. A compound of formula II

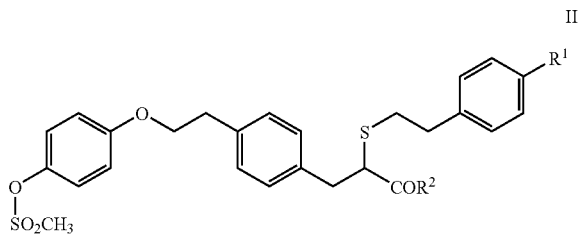

wherein $R^1$ represents chloro, fluoro or hydroxy and $R^2$ represents a protecting group for a carboxylic hydroxy group.

11. A compound of formula III

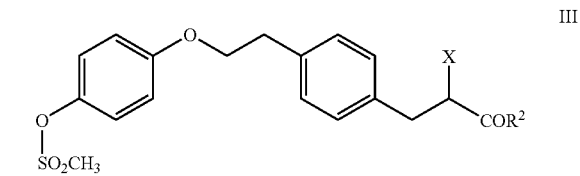

in which $R^2$ represents a protecting group for a carboxylic hydroxy group and X is a leaving group.

12. A pharmaceutical composition comprising a compound as claimed in any one of claims 1 to 5 combined with another PPAR modulating agent.

13. A pharmaceutical composition comprising a compound as claimed in any one of claims 1 to 5 combined with a cholesterol-lowering agent.

14. A pharmaceutical composition comprising a compound as claimed in any one of claims 1 to 5 combined with a HMG-CoA reductase inhibitor.

15. A pharmaceutical composition comprising a compound as claimed in any one of claims 1 to 5 combined with atorvastatin or a pharmaceutically acceptable salt, solvate, crystalline form or prodrug thereof.

16. A pharmaceutical composition comprising a compound as claimed in any one of claims 1 to 5 combined with rosuvastatin or a pharmaceutically acceptable salt thereof.

17. A pharmaceutical composition comprising a compound as claimed in any one of claims 1 to 5 combined with an IBAT inhibitor.

18. A pharmaceutical composition according to claim 17 wherein the IBAT inhibitor is selected from one of:

1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine; and 1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

* * * * *